(12) United States Patent
Krohn et al.

(10) Patent No.: US 8,857,261 B2
(45) Date of Patent: Oct. 14, 2014

(54) SENSING DEVICE AND METHOD OF ATTACHING THE SAME

(75) Inventors: Matthew Harvey Krohn, Reedsville, PA (US); Paul Aloysius Meyer, McVeytown, PA (US); Nathan John Smith, Lewistown, PA (US); Fred Timothy Matthews, Boalsburg, PA (US)

(73) Assignee: General Electric Company, Schenectady, NY (US)

( * ) Notice: Subject to any disclaimer, the term of this patent is extended or adjusted under 35 U.S.C. 154(b) by 233 days.

(21) Appl. No.: 13/445,598

(22) Filed: Apr. 12, 2012

(65) Prior Publication Data
US 2013/0269437 A1     Oct. 17, 2013

(51) Int. Cl.
*G01N 29/04*     (2006.01)

(52) U.S. Cl.
USPC ............................................. 73/587

(58) Field of Classification Search
USPC ...................... 73/588, 587, 582; 156/60, 295
See application file for complete search history.

(56) References Cited

U.S. PATENT DOCUMENTS

| | | | |
|---|---|---|---|
| 4,926,875 A | 5/1990 | Rabinovitz et al. | |
| 5,184,516 A * | 2/1993 | Blazic et al. | 73/799 |
| 5,262,696 A | 11/1993 | Culp | |
| 5,325,012 A | 6/1994 | Sato et al. | |
| 5,327,895 A | 7/1994 | Hashimoto et al. | |
| 5,548,179 A | 8/1996 | Kaida | |
| 5,834,877 A | 11/1998 | Buisker et al. | |
| 5,923,115 A | 7/1999 | Mohr, III et al. | |
| 5,998,786 A * | 12/1999 | Movaghar et al. | 250/239 |
| 6,110,314 A | 8/2000 | Nix et al. | |
| 6,256,118 B1 * | 7/2001 | Moriarty et al. | 358/483 |
| 6,467,140 B2 | 10/2002 | Gururaja | |
| 6,490,228 B2 | 12/2002 | Killam | |
| 6,538,363 B2 | 3/2003 | Nagahara et al. | |
| 6,640,634 B2 | 11/2003 | Hashimoto et al. | |
| 6,789,427 B2 | 9/2004 | Batzinger et al. | |
| 6,822,376 B2 | 11/2004 | Baumgartner | |
| 6,915,547 B2 | 7/2005 | Takeuchi et al. | |
| 6,925,869 B2 | 8/2005 | Senibi et al. | |

(Continued)

FOREIGN PATENT DOCUMENTS

| | | |
|---|---|---|
| EP | 0959617 A2 | 11/1999 |
| JP | 2008173790 A | 7/2008 |
| WO | WO-2006083245 A1 | 8/2006 |

OTHER PUBLICATIONS

Multi-layered PZT/polymer composites to increase signal-to-noise ratio and resolution for medical ultrasound transducers, Mills, D.M. Smith et al. vol. 46, Issue 4, Issue date—Jul. 1999, 2 pages.

(Continued)

*Primary Examiner* — Hezron E Williams
*Assistant Examiner* — Xin Zhong
(74) *Attorney, Agent, or Firm* — Hiscock & Barclay LLP

(57) ABSTRACT

A sensing device and a method of attaching the sensing device to a target object is disclosed. The substrate of the sensing device has one or more bonding material vias that allows the bonding material used to attach the substrate to the target object to flow from one side of the substrate to the other side of the substrate. The bonding material forms rivets to secure the substrate to the target object and to secure the layers of the substrate to each other.

18 Claims, 2 Drawing Sheets

(56) References Cited

U.S. PATENT DOCUMENTS

| | | |
|---|---|---|
| 7,017,245 B2 | 3/2006 | Baumgartner et al. |
| 7,082,655 B2 | 8/2006 | Yetter et al. |
| 7,148,608 B2 | 12/2006 | Baumgartner et al. |
| 7,156,938 B2 | 1/2007 | Baumgartner et al. |
| 7,291,110 B2 | 11/2007 | Sahatjian |
| 7,293,461 B1 | 11/2007 | Girndt |
| 7,322,243 B2 | 1/2008 | Liu et al. |
| 7,387,033 B2 | 6/2008 | Qing et al. |
| 7,395,189 B2 | 7/2008 | Qing et al. |
| 7,413,919 B2 | 8/2008 | Qing et al. |
| 7,573,181 B2 | 8/2009 | Rhim et al. |
| 7,581,296 B2 | 9/2009 | Yetter et al. |
| 7,668,667 B2 | 2/2010 | Robb et al. |
| 7,687,976 B2 | 3/2010 | Haider et al. |
| 7,696,671 B2 | 4/2010 | Sawada et al. |
| 8,361,901 B2 * | 1/2013 | Vick et al. .................... 438/667 |
| 2002/0051848 A1 | 5/2002 | Li |
| 2005/0061076 A1 * | 3/2005 | Kim ............................... 73/587 |
| 2006/0154398 A1 | 7/2006 | Qing et al. |
| 2007/0012111 A1 * | 1/2007 | Kim ............................... 73/594 |
| 2007/0143064 A1 * | 6/2007 | Boran et al. .................. 702/141 |
| 2007/0167765 A1 | 7/2007 | Unger et al. |
| 2007/0182594 A1 | 8/2007 | Face et al. |
| 2008/0155357 A1 | 6/2008 | Yu et al. |
| 2009/0039738 A1 | 2/2009 | Angelsen et al. |
| 2009/0056199 A1 * | 3/2009 | Reed .............................. 43/131 |

OTHER PUBLICATIONS

Search Report and Written Opinion from PCT/US2013/031401 dated Jun. 18, 2013.

* cited by examiner

US 8,857,261 B2

SENSING DEVICE AND METHOD OF ATTACHING THE SAME

BACKGROUND OF THE INVENTION

The subject matter disclosed herein relates to a sensing device attached to a target object using a bonding material.

Several industries (e.g., oil and gas, refinery, chemical, power generation) require the transport of fluid (e.g., liquids or gases) through pipes. Nondestructive testing systems can be placed on the outer surface of these pipes to monitor corrosion/erosion of the pipes, including corrosion/erosion on the interior of pipe walls. In some nondestructive testing systems, the probe or other nondestructive testing device is permanently coupled to the outer surface of the pipe to continuously monitor corrosion/erosion at that location to determine pipe corrosion/erosion rates and to determine whether that pipe location is in need of preventative maintenance to prevent a pipe failure.

One example of a nondestructive testing system used to monitor corrosion/erosion of a pipe is an ultrasonic testing system. When conducting ultrasonic testing of a pipe, an ultrasonic pulse is emitted from a probe coupled to the outer surface of the pipe and passed through the pipe. As the ultrasonic pulse passes into and through the pipe, various pulse reflections called echoes are reflected back to the probe as the pulse interacts with the outer surface of the pipe, internal structures, voids or occlusions within the pipe, and with the inner surface (or back wall) of the pipe. The echo signals can be displayed on a screen with echo amplitudes appearing as vertical traces and time of flight or distance as horizontal traces. By tracking the time difference between the transmission of the ultrasonic pulse and the receipt of the echoes, various characteristics of the pipe can be determined, including pipe thickness. If the thickness of the pipe at the location of the ultrasonic testing system decreases over time (e.g., as would be shown be a reduction in the time of flight of the back wall echo), this can be an indication of corrosion/erosion.

In an ultrasonic testing system, the substrate of a piezoelectric sensing device is attached to the outer surface of a pipe using a bonding material. The bonding material provides mechanical adhesion and forms a thin bond line between the piezoelectric sensing device and the pipe. Once cured, the bonding material holds the substrate to the pipe. In some installations, when the piezoelectric sensing device is attached to the pipe, the bond line formed by the bonding material is too thick, degrading the performance of the piezoelectric sensing device. The bond to the pipe formed by the bonding material, or the lamination between the layers of the substrate, are subject to failure, especially when the piezoelectric sensing device is inadvertently contacted from the side, causing the substrate to peel off of the pipe or a laminated layer to peel off of the substrate.

The discussion above is merely provided for general background information and is not intended to be used as an aid in determining the scope of the claimed subject matter.

BRIEF DESCRIPTION OF THE INVENTION

A sensing device and a method of attaching the sensing device to a target object is disclosed. The substrate of the sensing device has a one or more bonding material vias that allows the bonding material used to attach the substrate to the target object to flow from one side of the substrate to the other side of the substrate. The bonding material forms rivets to secure the substrate to the target object and to secure the layers of the substrate to each other. An advantage that may be realized in the practice of some of the disclosed embodiments of the piezoelectric sensing device having the bonding material vias is improved resistance to bond failure and delamination, and improved bond line formation.

In one embodiment, a sensing device is disclosed. The sensing device comprises a substrate for attachment to a surface of a target object using a bonding material, the substrate comprising a first side and a second side, one or more sensing elements located on the substrate, and one or more bonding material vias extending from the first side of the substrate to the second side of the substrate, wherein the bonding material vias are configured to allow the bonding material to flow from the second side of the substrate to the first side of the substrate and form bonding rivets on the first side of the substrate.

In another embodiment, a sensing device for inspecting a target object is disclosed. The sensing device comprises a substrate comprising a first side and a second side, the substrate comprising one or more bonding material vias extending from the first side of the substrate to the second side of the substrate, one or more sensing elements located on the substrate, and bonding material between the second side of the substrate and the surface of the target object and extending from the second side of the substrate to the first side of the substrate through the one or more bonding material vias, forming bonding rivets on the first side of the substrate.

In yet another embodiment, a method of attaching a sensing device to a surface of a target object, the sensing device having a substrate with one or more bonding material vias, is disclosed. The method comprises the steps of applying a bonding material to a second side of the substrate, pressing the substrate against the surface of the target object causing the bonding material to disperse along the second side of the substrate and through the one or more bonding material vias to form one or more bonding rivets on a first side of the substrate, and maintaining pressure to the first side of the substrate while the bonding material cures.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
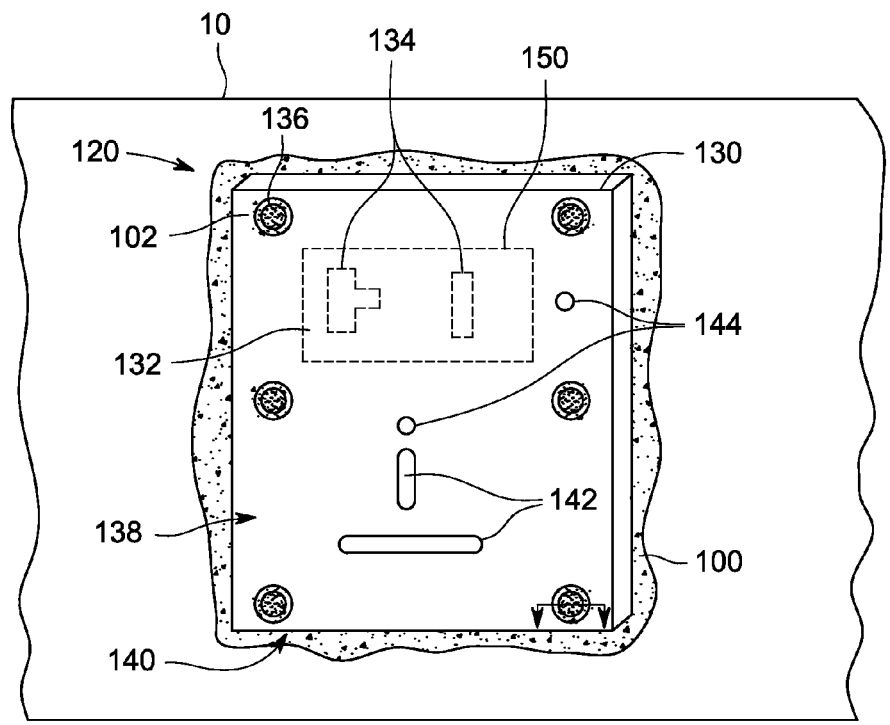
FIG. 1 is a schematic diagram of an exemplary embodiment of a sensing device affixed to a target object.
Figure 2:
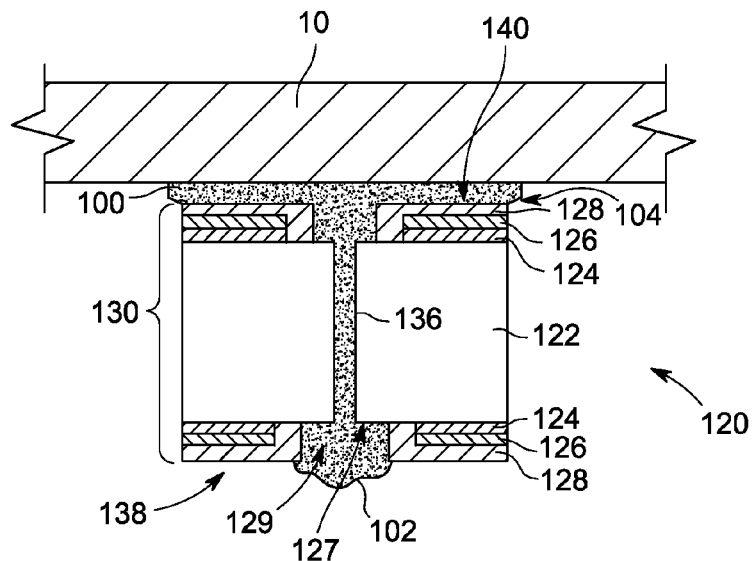
FIG. 2 is a cross-sectional view of an exemplary bonding material via of the sensing device shown in FIG. 1.

Referring now to the figures, FIG. 1 is a schematic diagram of an exemplary embodiment of a sensing device 120 affixed to a target object 10 with bonding material 100. FIG. 2 is a cross-sectional view of an exemplary bonding material via 136 of the substrate 130 of the sensing device 120 shown in FIG. 1. As will be explained, the bonding material 100 flows through one or more bonding material vias 136 in the sensing device 120 to form bonding rivets 102. Once cured, the bonding rivets 102 help to prevent the substrate 130 of the sensing device 120 from delaminating or from peeling off the target object 10.

As shown in FIG. 1, the sensing device 120 is disposed on the target object 10, such as a pipe, a tube, or related conduits that can be subject to corrosion and erosion by way of the fluid that is transported therein. In one embodiment, the sensing device 120 is part of an ultrasonic inspection system and includes a sensing element in the form of a piezoelectric element 150 (e.g., a ceramic piezoelectric transducer). It will be understood that other types of sensing devices and sensing elements can be used.

The substrate 130 of the sensing device 120 has a first side (or back side) 138 and a second side (or front side) 140, with the second side 140 of the substrate 130 placed against the target object 10. A receiving area 132 is located on the second side 140 of the substrate 130 in which a piezoelectric element 150 is located. The receiving area 132 also has electrodes 134 used for connecting the piezoelectric element 150 to the substrate 130. The sensing device 120 can also comprise one or more cable connector pads 142 coupled to the electrodes 134 through the connection vias 144 in the substrate 130. These connector pads 142 can be used to attach cables for connecting the piezoelectric element 150 to electronic equipment that monitors the sensing device 120.

In the embodiment shown in FIGS. 1 and 2, the sensing device 120 comprises a substrate 130 that is a flexible circuit comprising a plurality of different layers. In one embodiment, the substrate 130 can comprise a flexible circuit having a plurality of different layers, including a double-sided copper-cladded core, including a pure polyimide C-stage core 122 between copper layers 124. As a C-stage material, the core 122 is fully cured and is therefore relatively insoluble and infusible. In one embodiment, the core 122 can be 0.005 in. (0.127 mm) thick. In one embodiment, the copper layers 124 can be 0.0007 in. (0.0178 mm) thick. To facilitate soldering, the copper layers 124 can be plated with plating layers 126. The plating can be 0.0005 in. (0.0127 mm) thick. In one embodiment, electrolysis nickel over immersion gold (ENIG) is used to plate the copper layers 124. In one embodiment, the substrate 130 has glass reinforced polyimide C-stage cover layers 128 formed over the copper layers 124 and the plating layers 126. The glass reinforcement can be woven fibreglass with a 1080 glass type. The pure polyimide C-stage core 122 and the glass reinforced polyimide C-stage cover layers 128 provide the flexibility and support necessary for the substrate 130 to be installed on curved surfaces of a pipe or other circumferential devices.

In one embodiment, the glass reinforced polyimide C-stage cover layers 128 can be formed over the copper layers 124 by providing glass-reinforced polyimide B-stage sheets on the pure polyimide C-stage core 122, which can also be provided in a sheet, and compressing the polyimide layers between two presses while exposing the layers to temperatures that will form the substrate 130 after lamination. It will be understood that the layers of the substrate 130 in other embodiments can include other materials such as a polyester (PET), polyethylene napthalate (PEN), and polyetherimide (PEI). After lamination, these layers of the substrate 130 can undesirably delaminate if one layer is pulled away from, or in an opposite direction than, an adjacent layer.

In order to help prevent delamination of the substrate and to prevent failure of the bond between the substrate 130 and the target object 10, as shown in FIGS. 1 and 2, the sensing device 120 has a plurality of bonding material vias 136 extending from the first side 138 to the second side 140 of the substrate 130. During installation, when the substrate 130 of the sensing device 120 is pressed against the target object 10, the bonding material vias 136 allow the bonding material 100 to flow through the substrate 130 and form bonding rivets 102 on the first side 138 of the substrate 130. After the bonding material 100 cures, the bonding rivets 102 help to prevent the substrate 130 of the sensing device 120 from delaminating or from peeling off the target object 10. In one embodiment, the bonding materials vias 136 have a diameter of 0.005 in (1.27 mm). As shown in FIG. 2, windows 129 can be formed in the cover layers 128 of the substrate 130 around the bonding material vias 136, forming ledges 127 against which the bonding rivets 102 can rest, securing the substrate 130 to the bonding material 100 and the target object 10. The number of bonding material vias 136 used for a sensing device 120 (e.g., one or more) can vary for different sensing devices 120.

The bonding material 100 affixes the sensing device 120 to the target object 10 and couples the sensing device 120 to the target object to, e.g., transfer ultrasonic signals. The bonding material 100 may be any suitable bonding material, including, but not limited to, one-part thermosettings, heat cured thermosettings, moisture cured thermosettings, two-part thermosettings, thermoplastics, cold-flow adhesives, epoxies, urethanes, polyimides, cyanoacrylates, urethanes, acrylics, silicones or hot melt adhesives. The bonding material 100 may be applied either to the second side 140 of the substrate 130 or directly to the surface of the target object 10. By pressing the substrate 130 against the target object 10, the bonding material 100 will flow through the bonding material vias 136 to form the bonding rivets 102. The bonding rivets 102 provide superior bonding strength to the target object 10 and decrease the risk of delamination of the substrate 130.

Figure 3:
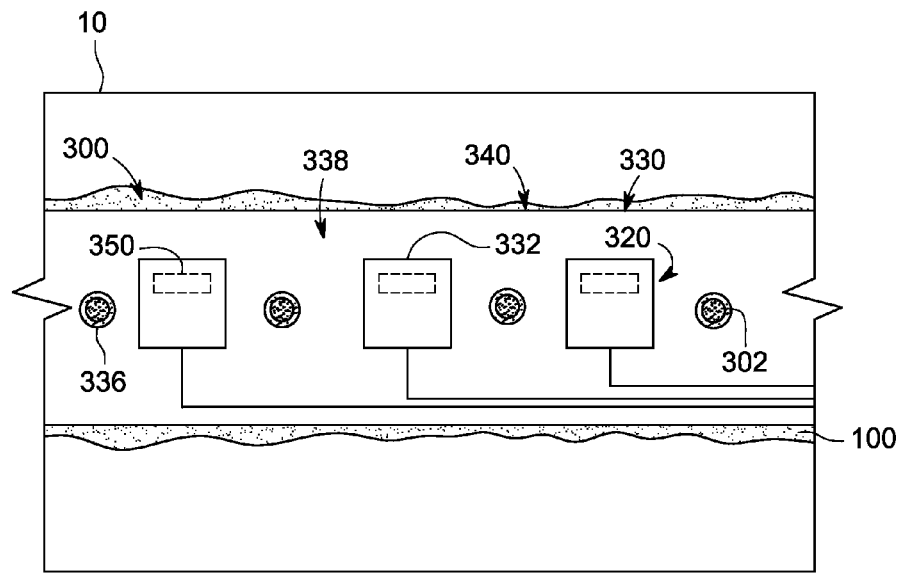
FIG. 3 is a schematic diagram of an exemplary embodiment of a strip sensor having a plurality of sensing devices on a substrate and affixed to a target object using a bonding material.

FIG. 3 is a schematic diagram of an exemplary embodiment of a strip sensor 300 having a plurality of sensing devices 320 on a substrate 330 and affixed to a target object 100 using a bonding material 100. In one embodiment, each of the sensing devices 320 have a piezoelectric element 350 disposed on a receiving area 332 of the substrate 330. The sensing devices 320 can be spaced apart from one another along the substrate 330, which can comprise flexible circuit that can conform to the shape of the target object 10. The substrate 330 of the strip sensor 300 has a number of bonding material vias 336 disposed therein. As discussed in the embodiments above, the bonding material vias 336 allow the bonding material 100 to flow from the second side 340 to the first side 338 of the substrate 300 to form bonding rivets 302.

Although the strip sensor 300 is depicted in FIG. 3 as a linear array (e.g., wherein the sensing devices 330 form a single row with one or more columns) other configurations are also envisioned. In one embodiment, the strip sensor 300 can include one or more rows and one or more columns of sensing devices 330. In another embodiment, the sensing devices 330 are arranged in formations that are different than arrays of rows and columns. By way of example, one formation for strip sensor 300 can comprise a first row of sensing devices 330 and a second row of sensing devices 330, wherein the second row is positioned in perpendicular relation to the first row, thus forming a "t" shape.

Figure 4:
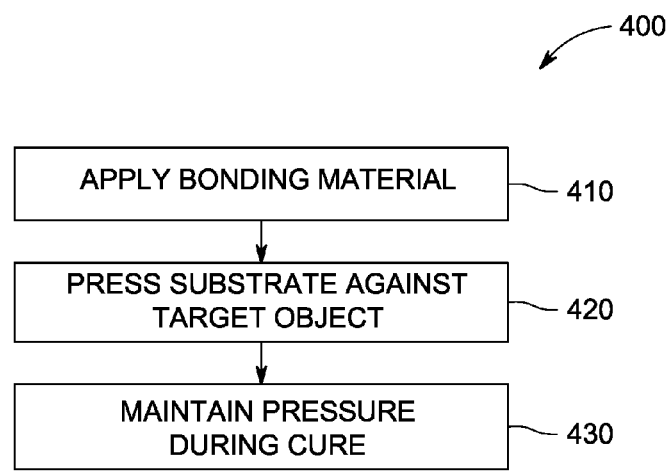
FIG. 4 is a flow diagram of an exemplary method for attaching a sensing device to a target object.

Turning now to FIG. 4, an exemplary method 400 of attaching a sensing device to a surface of a target object is shown. The sensing device as described above has a substrate with one or more bonding material vias. At step 410, the bonding material is applied to a second side of the substrate. At step 420, the substrate is then pressed against the surface of the target object causing the bonding material to disperse along the second side of the substrate and through the bonding material vias to form bonding rivets on a first side of the substrate. At step 430, pressure is applied to the first side of the substrate while the bonding material cures.

This written description uses examples to disclose embodiments of the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A sensing device comprising:
   a substrate for attachment to a surface of a target object using a bonding material, the substrate comprising a first side and a second side;
   one or more sensing elements located on the substrate;
   one or more bonding material vias extending from the first side of the substrate to the second side of the substrate, wherein the bonding material vias are configured to allow the bonding material to flow from the second side of the substrate to the first side of the substrate and form bonding rivets on the first side of the substrate; and
   at least one layer on the first side of the substrate forming a window around each of the one or more bonding material vias and limiting the flow of the bonding material across the first side of the substrate within the window, wherein the at least one layer includes a material selected from the group consisting of polyimide, glass reinforced polyimide, copper, plating, electrolysis nickel over immersion gold, polyester, polyethylene naphthalate, and polyetherimide.

2. The sensing device of claim 1, wherein the one or more sensing elements are located on the second side of the substrate.

3. The sensing device of claim 1, wherein the substrate is a flexible circuit.

4. The sensing device of claim 1, wherein a diameter of the window around each of the one or more bonding material vias is greater than a diameter of its corresponding bonding material via.

5. The sensing device of claim 1, wherein the at least one layer includes a glass-reinforced polyimide layer formed over a copper layer.

6. The sensing device of claim 1, wherein the one or more sensing elements are piezoelectric elements.

7. The sensing device of claim 6, wherein the piezoelectric elements are ceramic piezoelectric transducers.

8. A sensing device for inspecting a target object, the sensing device comprising:
   a substrate comprising a first side and a second side, the substrate comprising one or more bonding material vias extending from the first side of the substrate to the second side of the substrate;
   at least one layer on the first side of the substrate forming a window around each of the one or more bonding material vias, wherein the at least one layer includes a material selected from the group consisting of polyimide, glass reinforced polyimide, copper, plating, electrolysis nickel over immersion gold, polyester, polyethylene naphthalate, and polyetherimide,
   one or more sensing elements located on the substrate; and
   bonding material between the entire second side of the substrate and the surface of the target object and extending from the second side of the substrate to the first side of the substrate through the one or more bonding material vias, forming bonding rivets on the first side of the substrate by covering a portion of the first side of the substrate adjacent the one or more bonding material vias.

9. The sensing device of claim 8, wherein the one or more sensing elements are located on the second side of the substrate.

10. The sensing device of claim 8, wherein the substrate is a flexible circuit.

11. The sensing device of claim 8, wherein the bonding material is selected from the group consisting of heat cured thermosettings, moisture cured thermosettings, two-part thermosettings, thermoplastics, cold-flow adhesives, epoxies, urethanes, polyimides, cyanoacrylates, urethanes, acrylics, silicones and hot melt adhesives.

12. The sensing device of claim 8, wherein the at least one layer includes a glass-reinforced polyimide layer formed over a copper layer.

13. The sensing device of claim 8, wherein one or more sensing elements are piezoelectric elements.

14. The sensing device of claim 13, wherein the piezoelectric elements are ceramic piezoelectric transducers.

15. A method of attaching a sensing device to a surface of a target object, the sensing device having a substrate with one or more bonding material vias, the method comprising the steps of:
   forming a layer on the first side of the substrate around each of the one or more bonding material vias, wherein the at least one layer includes a material selected from the group consisting of polyimide, glass reinforced polyimide, copper, plating, electrolysis nickel over immersion gold, polyester, polyethylene naphthalate, and polyetherimide;
   disposing a bonding material between a second side of the substrate and the surface of the target object;
   pressing the substrate and the bonding material against the surface of the target object causing the bonding material to disperse along the second side of the substrate and to flow through the one or more bonding material vias and onto a first side of the substrate to form one or more bonding rivets on the first side of the substrate, wherein the step of pressing the substrate includes causing the bonding material to contact the entire second side of the substrate; and maintaining pressure to the first side of the substrate while the bonding material cures.

16. The method of claim 15, wherein the step of pressing the substrate further includes causing the bonding material to flow across the first side of the substrate including contacting the layer around each of the one or more bonding material vias.

17. The method of claim 15, wherein the layer on the first side of the substrate around each of the one or more bonding material vias comprises an opening having a diameter larger than a diameter of each of the one or more bonding material vias.

18. The method of claim 15, wherein the layer includes a glass-reinforced polyimide sheet and the forming-layer step includes disposing the glass-reinforced polyimide sheet over the first side of the substrate and laminating the glass-reinforced polyimide sheet to the substrate.

* * * * *